US006992278B2

(12) United States Patent
Sjoberg et al.

(10) Patent No.: US 6,992,278 B2
(45) Date of Patent: Jan. 31, 2006

(54) HOMING PROCESS (75) Inventors: Jan Sjoberg, Uppsala (SE); Rony Wiberg, Heby (SE); Goran Wahlberg, Vasteras (SE)

(73) Assignee: Gyros AB, Uppsala (SE)

( * ) Notice: Subject to any disclaimer, the term of this patent is extended or adjusted under 35 U.S.C. 154(b) by 275 days.

(21) Appl. No.: 10/408,352

(22) Filed: Apr. 8, 2003

(65) Prior Publication Data

US 2003/0231312 A1 Dec. 18, 2003

Related U.S. Application Data

(60) Provisional application No. 60/370,234, filed on Apr. 8, 2002.

(30) Foreign Application Priority Data

Apr. 8, 2002 (CH) .................................. 0201072

(51) Int. Cl.
*G01D 5/34* (2006.01)
*G01J 9/00* (2006.01)
(52) U.S. Cl. .......................... 250/231.17; 250/231.13; 250/231.14; 356/620; 702/46; 702/49
(58) Field of Classification Search ........... 250/231.13, 250/231.14, 231.16, 231.17, 231.18, 559.41, 250/559.44; 341/11, 13; 356/430, 620; 702/31, 46, 49, 100
See application file for complete search history.

(56) References Cited

U.S. PATENT DOCUMENTS 4,456,581 A * 6/1984 Edelmann et al. ............ 422/72

| 5,892,577 | A | | 4/1999 | Gordon |
| 5,932,874 | A | * | 8/1999 | Legg et al. ............. 250/231.13 |
| 6,221,226 | B1 | * | 4/2001 | Kopf-Sill .................... 204/602 |
| 6,407,379 | B1 | * | 6/2002 | Shinbo .................. 250/231.13 |
| 6,450,044 | B1 | * | 9/2002 | Eisenhauer et al. .... 73/862.193 |
| 2004/0259237 | A1 | * | 12/2004 | Kellogg et al. .......... 435/287.1 |

FOREIGN PATENT DOCUMENTS

| EP | 0 693 560 A2 | 1/1996 |
| WO | WO 97/01085 A1 | 1/1997 |
| WO | WO 00/79285 A2 | 12/2000 |
| WO | WO 01/46465 A2 | 6/2001 |
| WO | WO 01/46465 A3 | 6/2001 |
| WO | WO 01/55711 A1 | 8/2001 |

* cited by examiner

*Primary Examiner*—David Porta
*Assistant Examiner*—Davienne Monbleau
(74) *Attorney, Agent, or Firm*—Birch, Stewart, Kolasch & Birch, LLP (57) ABSTRACT

The present invention relates to a method for determining a home position by means of a home position mark on a special microfluidic device type used in a microfluidic system. The method for determining a home position by means of a home position mark on a microfluidic device used in a microfluidic system comprising at least one programmable controller having storage means, a position device being able to communicate with the controller, and a home position mark detector connected to said controller, wherein said method comprises the following steps: scanning a disc for mark edges; rejecting false home mark(s) and identifying a correct home position mark; and determining a home position by use of mark edges of the correct home position mark identified in the previous step. The present invention also relates to a microfluidic system and a computer program product and a computer program product on a computer usable medium.

28 Claims, 6 Drawing Sheets

HOMING PROCESS

This application claims the benefit of Provisional Application No. 60/370,234, filed Apr. 8, 2000.

TECHNICAL FIELD

The present invention relates to a homing process in a microfluidic system.

More specifically, the present invention relates to a homing process for determining the home position by means of a home position mark of a special microfluidic device type used in a microfluidic system. The present invention also relates to a microfluidic system and a computer program product and a computer program product on a computer usable medium.

BACKGROUND OF THE INVENTION

The term "microfluidic" refers to a system or device having one or a network of enclosed chambers and/or channels, which have micro scale dimensions, e.g., having at least one cross sectional dimension in the range from about 0,1 $\mu$m to about 500 $\mu$m. The term "microfluidic" in the context of device, system, disc etc refers to the fact that liquid volumes in the $\mu$l-range are transported within the system. This means that there may or may not be liquid transport within a certain part of the system, for instance the microfluidic device/disc. The $\mu$l-range includes the nl-range as well as the pico-litre range. Microfluidic substrates are often fabricated using photolithography, wet chemical etching, injection-molding, embossing, and other techniques similar to those employed in the semiconductor industry. The resulting devices can be used to perform a variety of sophisticated chemical and biological analytical techniques.

Microfluidic analytical systems have a number of advantages over conventional chemical or physical laboratory techniques. For example, microfluidic systems are particularly well adapted for analyzing small sample sizes, typically making use of samples on the order of nanoliters and even picoliters. The channel defining substrates may be produced at relatively low cost, and the channels can be arranged to perform numerous analytical operations, including mixing, dispensing, valving, reactions, detections, electrophoresis, and the like. The analytical capabilities of microfluidic systems are generally enhanced by increasing the number and complexity of network channels, reaction chambers, and the like.

Substantial advances have recently been made in the general areas of flow control and physical interactions between the samples and the supporting analytical structures.

Flow control management may make use of a variety of mechanisms, including the patterned application of voltage, current, or electrical power to the substrate (for example, to induce and/or control electrokinetic flow or electrophoretic separations). Alternatively, fluid flows may be induced mechanically through the application of differential pressure, acoustic energy, or the like. Selective heating, cooling, exposure to light or other radiation, or other inputs may be provided at selected locations distributed about the substrate to promote the desired chemical and/or biological interactions. Similarly, measurements of light or other emissions, electrical/electrochemical signals, and pH may be taken from the substrate to provide analytical results. As work has progressed in each of these areas, the channel size has gradually decreased while the channel network has increased in complexity, significantly enhancing the overall capabilities of microfluidic systems.

The microfluidics technologies/devices are capable of controlling and transferring tiny quantities of liquids to allow biological assays to be integrated and accomplished on a small scale.

Microfluidics is the miniaturization of biological separation and assay techniques to such a degree that multiple "experiments" can be accomplished on a "chip" small enough to fit in the palm of your hand. Tiny quantities of solvent, sample, and reagents are steered through narrow channels on the chip, where they are mixed and analyzed by such techniques as electrophoresis, fluorescence detection, immunoassay, or indeed almost any classical laboratory method.

Today a number of products varying in many respects are available. Laboratory chips may be made from plastic, glass, quartz or even silicon. The fluid may be driven by centrifugal forces, mechanical pressure or vacuum pumps, by inertia, or by one of several electrical methods; fluid flow can be diverted around the chip by mechanical valves, surface tension, voltage gradients, or even electromagnetic forces.

In the technique of using centrifugal forces to drive the fluid a disc that can be spun is used. Some discs have been of the same physical format as conventional CDs. Samples are placed near the center of the disc and centrifugal forces, created as the disc rotates, push them out through channels cut into the plastic, circumventing the need to design sophisticated electrokinetic or mechanical pumping structures.

As will become evident in the forth-coming description the present invention is in particular applicable to (but not limited to) micro-analysis systems that are based on microchannels formed in a rotatable, usually plastic, disc, often called a "lab on a chip". Such discs can be used to perform analysis and separation on small quantities of fluids. In order to reduce costs it is desirable that the discs should be not restricted to use with just one type of reagent or fluid but should be able to work with a variety of fluids.

Furthermore it is often desirable during the preparation of samples that the disc permits the user to dispense accurate volumes of any desired combination of fluids or samples without modifying the disc. A microanalysis device for fluids provided in a rotatable disc is described e.g. in WO-0146465. A liquid transfer station has a robot that transfer at least one sample or any other predetermined liquid aliquot at a time from the sample and reagent station to a microfluidic device, for instance in the form of a disc that can be spun. The station have means for transfer of liquid samples, and other liquids, for instance a number of injection needles connected to syringe pumps or a number of solid pins may be used for the transfer of samples. Said needles and pins may be configured in different numbers of rows and columns having different distance between the tips in both directions. Another alternative is the microdispensor described in WO 9701085.

The needles or pins have to be exactly maneuvered to the inlet of each channel. The microfluidic discs may be designed in different ways and each microfluidic disc differs individually due to the manufacturing process. A home position mark is preferably placed in an outer circumferential zone outside the detection areas or in some other position, which can be detected with high accuracy. The position coordinates of each specific spot of the surface of the disc is given as the angular position relative to the home position mark and as the radial position relative to the circumference or axis of symmetry or relative to any other arbitrary fixed position on the disc.

The process or method for finding the home position mark and determining is called for "Homing the disc" and the "Homing" process. Known homing processes involves the scanning of the disc for finding an edge of the home position mark. A home position mark on a rotating disc placed on the disc holder is detected by a home position mark detector when a home mark is passing. It is supposed that the only detectable edges present on the disc is the edges of a home mark. However, many times the detected edge is an edge of a "false home mark". A defect or pollution are present in the outer circumferential zone outside the detection areas where the home position mark is located. Said defects and pollutions may also be interpreted as home position marks. The known homing process does not involve a check if a mark is a home mark or not, and any edge will be accepted to be a home mark. Said false marks cause problems and may ruin a whole microfluidic disc, as there is no possibility to locate the home position mark, and drive and place the needles properly.

BRIEF DESCRIPTION OF THE INVENTION

It is an object of the present invention to solve said problems with false "home position marks".

It is another object of the present invention to increase accuracy of a home position by means of a home position mark on a special microfluidic device type.

It is another object of the present invention to identify a true home position mark from false marks.

Further, it is an object of the invention to determine a correct position of the home position.

These objects are achieved by the claimed invention according to claims 1–21.

One advantage with the present invention is that the system will work faster and more properly, even though a lot of false marks are present on the disc that would have normally disturbed the homing process.

Another advantage is that the yield will increase as less microfluidic discs have to be discarded.

DETAILED DESCRIPTION OF THE INVENTION

The present invention relates to microfluidic systems.

Different microfluidic systems are known. One type of systems comprises a controller unit and a microfluidic instrument. Such a system is called a Stand Alone System. Each system has its own data and operates completely stand alone. The interaction with the system may be performed at an associated Personal Computer (PC).

Another system can be considered as a group of instruments plus a common persistent storage location, e.g. database. Many instruments can operate on the same set of data (Method Data, Microfluidic Device Data, etc). All interaction with the system needs to be performed at an instrument connected computer, a controller. This second system is often called a Distributed Database Solution.

In a third solution, the distributed solution, the system is considered as a group of instruments, a common storage persistent storage location (database), and a number of clients. With this solution the same functionality as in the above-mentioned Distributed Database Solution is reached. In addition there will be a possibility to interact with the system from non instrument connected computers. Examples of additional provided functionality are:

Remote monitoring of instruments.

Perform functions that are not instrument specific (Method

Development, Evaluation of processed data. Etc)

With this third solution it is possible to control (Start, Pause, Abort) the processing remotely, that is, from a non instrument connected computer.

An operator/user can control and monitor the performance of the microfluidic instrument from the controller. The microfluidic instrument comprises of a number of different stations, each station being capable of performing one or a number of defined operations. Different types of microfluidic instruments consist of different kinds of stations or number of stations. Therefore, some operations will not be provided for or applicable on a certain type of microfluidic instrument.

The operations are initiated from the controller.

Figure 1:
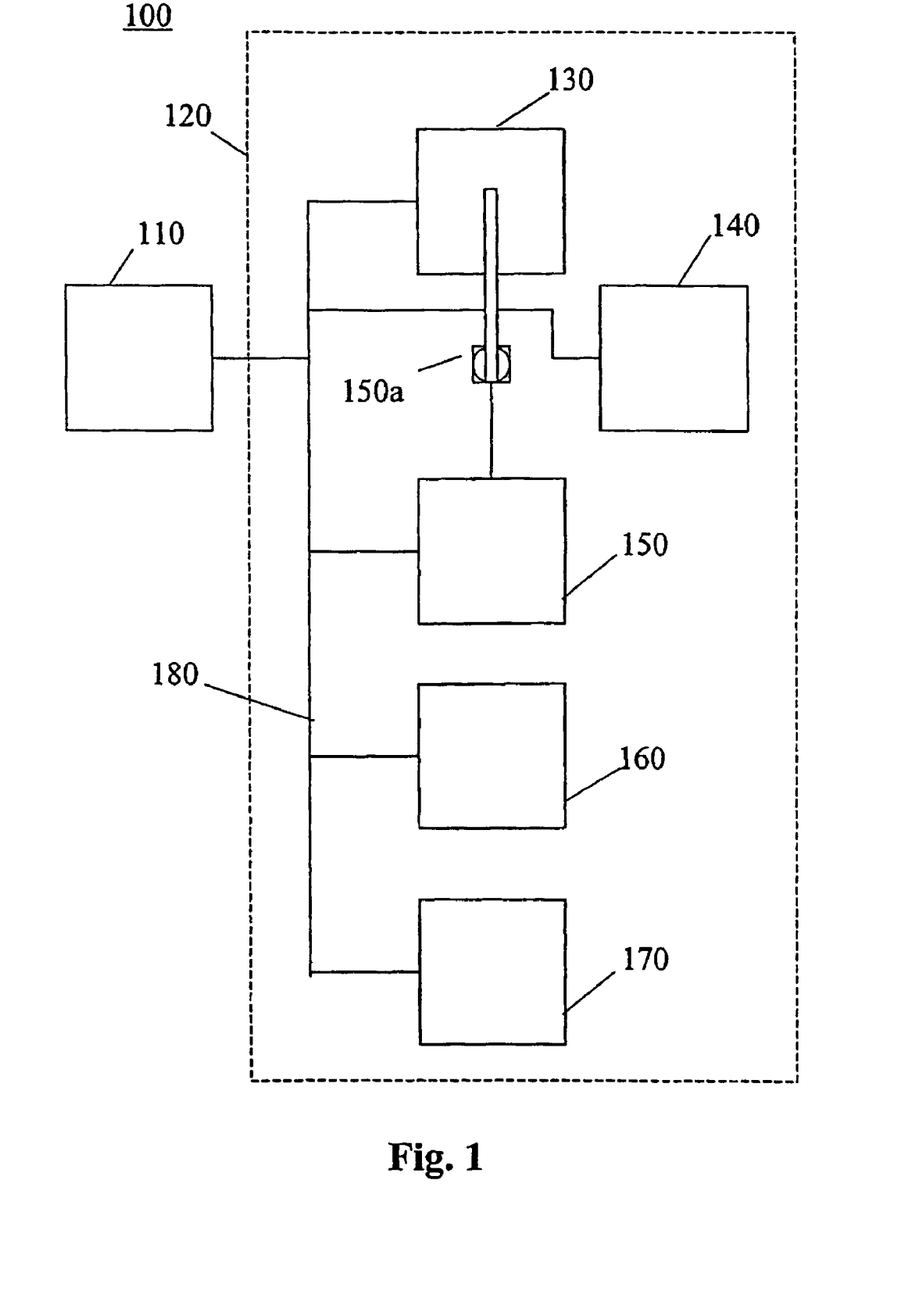
FIG. 1 is a block diagram depicting schematically a microfluidic system.

FIG. 1 is a block diagram depicting schematically a microfluidic system 100 that includes a control unit, also denoted controller, 110 and an instrument 120 comprising a sample and reagent station 130, a wash station 140, a liquid transfer station 150, at least one station 160 for implementing transport of liquid within the microfluidic device e.g., a spinner station and a detector station 170.

The controller 10 may be one or more computers outside the instrument and/or one or more central processors within the instrument. The controller is connected to the instrument 120 and its different stations via a conductor or data bus 180 and operation orders are transmitted either as electrical or optical signals or included in a suitable predetermined protocol to hardware circuits distributed between the stations.

A controller may comprise different control means, for instance electronic and programmable control means with operator's interface and software, not further disclosed, may be assigned to the detector arrangement among others for a) recognizing one or more pairs of start/stop-positions (angular and/or radial) for irradiating if the detection principle utilized requires irradiation and/or for collecting radiation, b) identifying individual subareas in detection areas or elsewhere in the surface of the disc, c) controlling the simultaneous rotating of the disc and the incremental radial displacement of a detector head, d) collecting radiation data from the detection areas/ detection microcavities, e) treatment and presentation of the collected data, and/or f) determining the time at which a particular angular position is in front of the objective of the detector head from the rotational speed.

Different parts of the arrangement may communicate with the controller 110. The controller will in the preferred variants instruct the detector head to successively collect radiation from distinct and pre-selected parts of the surface of the disc. Typically the controller is programmed to start collecting radiation at a position, primarily an angular and/or a radial position, which is prior to an intended detection area, and to end the collecting at a position, which is after the same detection area. Preferably the starting position and the ending position are at essentially the same radial distance. This means that the sub-areas from which radiation is collected primarily are located within detection areas. Yet further, in preferred variants, sub-areas close to the detection areas are also included. If the radiation requires that the substance is irradiated, which is the case if fluorescence is measured, the control means also defines the settings for the start and stop positions for irradiation. These latter settings are typically essentially the same as for collecting radiation.

The start and stop signals for collecting radiation is preferably directly linked to the angular positions in the disc at which collection is to start and end, respectively. This also includes that due account is taken for delays that may be inherent in the system or preset, i.e., the start and stop signals may have to be initiated before the focal area is positioned in front of the start and stop position, respectively. If an angular aligning system wihin the microfluidic system comprises an encoder, the encoder signals corresponding to a start position and a stop position are used to define the time period during which radiation is to be collected. In an alternative, the start and stop for collecting radiation is linked to a preset rotating speed, i.e., the controller calculates from a preset rotating speed the time at which the start and stop position should be in front of the objective.

The controller may be programmed to change the radial position of the detector head (focal area) after a predetermined number of revolutions of the disc, for instance after 1, 2 or more revolutions with preference for 1.

Further, the present system have a sample and reagent station 130 comprising means for storing samples, reagents or other liquids. Said samples, reagents or other liquids is stored in some kind of container, such as a micro plate or multiwell plate, a test tube rack or a test tube. Said plate is designed as a matrix of small containers or wells. Said plate can have different sizes depending on the number of wells. The container may be loosely fixed at a container holder, for instance a so called carousel, which is a circular revolving plate.

The liquid transfer station 150 has a robot 150a that transfer at least one sample or any other predetermined liquid aliquot at a time from the sample and reagent station 130 to a microfluidic device, for instance in the form of a disc that can be spun. The station have means for transfer of liquid samples, and other liquids, for instance a number of injection needles connected to syringe pumps or a number of solid pins may be used for the transfer of samples. Said needles and pins may be configured in different numbers of rows and columns having different distance between the tips in both directions. Another alternative is the microdispensor described in WO 9701085.

Said needles and pins may or may not be washed in a wash solution between the transfers of samples and reagents. Washing is done by means placed in a wash station 140.

The liquids dispensed to a microfluidic device are transported within the device by means associated with the station 160 for implementing liquid transport. This station may be a spinner station in case the the microfludic device is adapted to permit liquid transport caused by spinning. The result of a process carried out within the microfluidic device is determined by means for detecting (a detector) which is located in a detector station 170.

The arrangement of the detector station 170 is adapted for measuring radiation from a plurality of detection each of which is associated with a detection microcavity in a microfluidic. The arrangement comprises:

(a) a detector head with a focal area, and a disc holder which are linked to a means enabling for the detector head, i.e., the focal area to transverse, the surface of the disc when the disc is placed in the disc holder.

(b) an angular aligning system for recognizing the angular position of the part area which at a particular time is covered by the focal area, and (c) an optional radial aligning system for recognizing the radial position of the part area which at a particular time is covered by the focal area, and (d) a controller, e.g., computer with software, which controls
  (i) equipment causing the focal area to transverse the detection areas in an annular zone of the disc, and
  (ii) the detector head successively collects radiation in a preselected manner from individual subareas of essentially the same size as the focal area within at least one of the detection areas in said annular zone.

As shown in FIG. 1, each of said stations is connected to the controller 110 and controlled and monitored from the controller 110 by means of a number of operations. A software operation is defined as a logical group of hardware instructions, which are performed to accomplish a certain function, such as:

Implementing transport of liquid, for instance spinning the device if the device is in the form of a disc that can be spinned in order to induce liquid flow.

Sample transfer to a specific common distribution channel or a specific microstructure.

Reagent transfer to a specific common distribution channel or a specific microstructure.

Position the microfluidic device.

Incubate the liquids at a certain position in the microstructures for a specific time.

Detection, i.e. detection of the results of the method carried out in the microfluidic device.

An operation may consist of a number of steps. A step is a non-dividable instruction, such as a ramp in a spin operation. A set can be constituted by putting together a number of these operations in a desired order. Such a set is defined as a method and controls all parts conducted within the instrument. It prescribes a type of microfluidic device and defines a set of actions, operations. It may prescribe halting for conducting steps outside the instrument, for instance incubations at constant temperature when the method concerns cell culturing.

The present invention relates to a method for determining a home position by means of a home position mark on a special microfluidic device type used in a microfluidic system, as described above.

Figure 2:
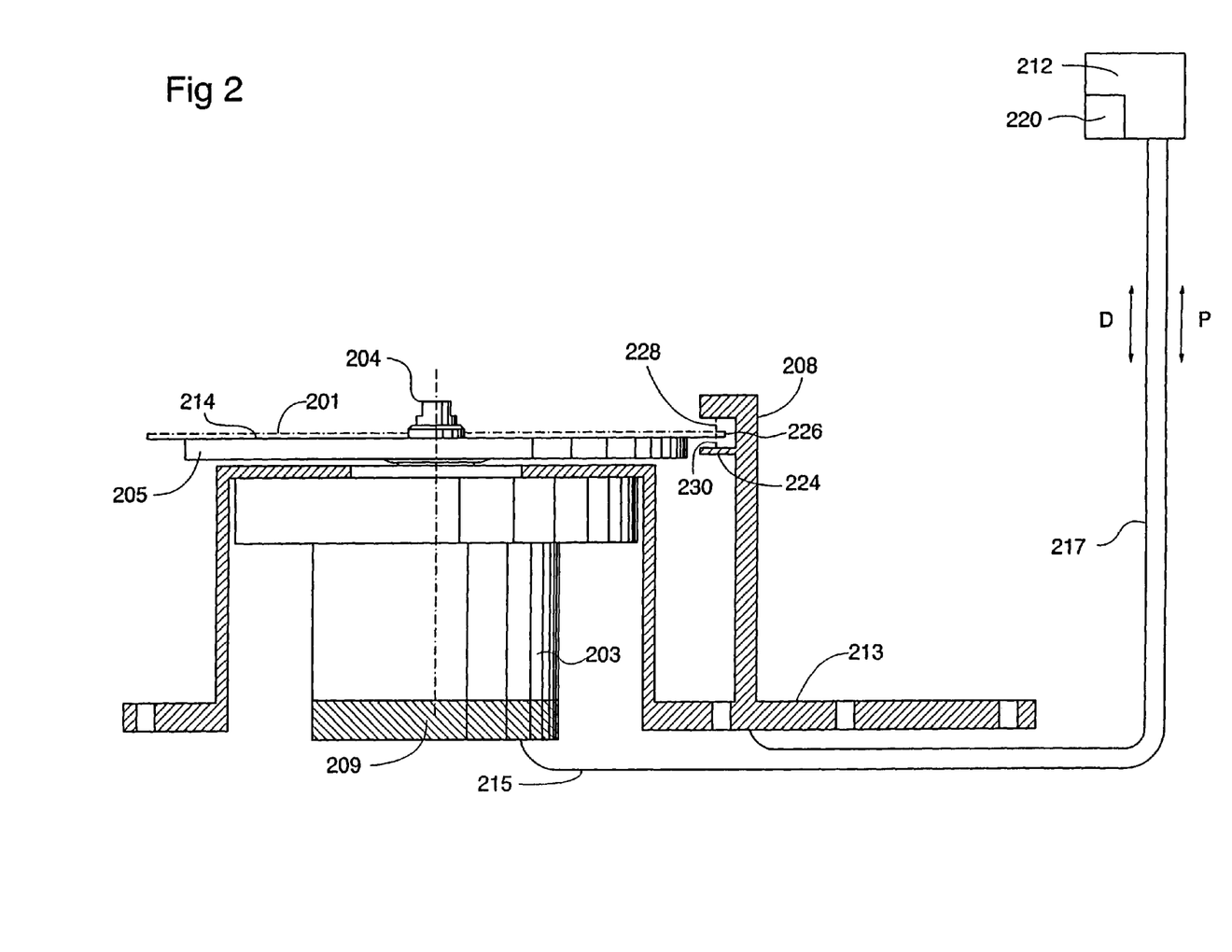
FIG. 2 shows a home position mark detector arrangement in a microfluidic system.

FIG. 2 shows a home position mark detector arranged with a spinner station in a microfluidic system. In a typical variant, a motor 203 (e.g., a spinner) with a rotatable shaft 204 carrying a disc holder 205 are supported on a frame structure 213. The motor 203 controls the rotating speed that can be varied, e.g., within an interval between 0–15,000 rpm, such as above 60 rpm. The rotation of the disc 201 may be stepwise. The disc holder 205 is preferably a plate on which the disc can be placed. The disc holder could also be a device that holds the disc at its periphery. In order to reduce wobbling of the disc (if the disc is skewed), the side 214 of the plate facing the disc may comprise a system of evenly distributed uncovered shallow grooves or channel openings that are connected to a vacuum system by which the disc can be sucked to the plate. See for instance WO-03025549, which is incorporated herein by reference.

The system also has to contain a position device 209 for determining when a predetermined angular position of the disc is in front of a needle or an detector objective of the system. Different position devices are known in the market, such as encoders, absolute position encoders etc. A simple but less accurate alternative is to include calculating means that calculates the time needed from a preset rotation speed and the angular distance between the predetermined position and a home position mark (i.e., from the preset rotation speed and the angular position co-ordinate). This kind of calculating means may be associated with the controller.

An absolute encoder is a position device that progressively gives the angular distance from the home position mark while the disc is rotating.

The position device 209 is typically associated with the motor 203, the shaft 204, and the disc holder 205 and it is connected to a position controlling means of the controller. By associating the position device directly with the disc 201 it is likely that the most accurate determination will be accomplished. The position device typically divides each revolution of the shaft into a large number of grades, denoted as resolution grades, for instance >5,000, such as >10,000 or >20,000 or >30,000. The position device should be able to give the angular position coordinate for the part of the disc which is in front of a home position mark detector with an accuracy and resolution of ±1°, such as within ±0.1° or within ±0.01° (provided there are 360° per revolution). The exact accuracy needed will depend on the size of the disc, radial position of the detection area, the required sensitivity, size of detection area, etc The position controlling means 220 of the controller 212 will receive or transmit different data using a position signal P over the connection 215 depending on the type of position device 209. If the position device is an encoder generating a pulse for each resolution grade, the position controlling means involves a pulse counter for registering the pulse sum value that is representing the current position of the disc relative to a start position or the home position, and the detector. If the position device is an absolute encoder, the position controlling means will receive or transmit an absolute measure of the angular distance from a start position or the home position. In either case, the position controlling means of the controller is able to control the position device. The position controlling means sets a desired position and transfer the desired value to the position device, which receives the position and controls the motor 203, the shaft 204, and the disc holder 205 to set the disc in the desired position.

On each microfluidic disc 201 is a home position mark (310 in FIG. 3) preferably placed in an outer circumferential zone outside the detection areas or in some other position. The home position mark must have at least one characteristic feature that is detectable, preferably with high accuracy, and possible to identify for the controller and the microfluidic system. Such a characteristic feature may be the angular length of the mark, denioted $L_{mark}$. The position coordinates of each specific spot of the surface of the disc is given as the angular position relative to the home position mark and as the radial position relative to the circumference or axis of symmetry or relative to any other arbitrary fixed position on the disc.

A home position mark detector 208 typically has a fixed position outside the disc, for instance on the frame structure 213. A home position mark detector 208 is capable of detecting when a home position mark (305 in FIG. 3) is passing.

In the embodiment illustrated in FIG. 2, the home position mark detector 208 comprises an electromagnetic beam source 222 and a transducer arrangement 224. The outer circumference of the disc is placed in the gap 226 between two optical fibres, the source fibre 228 and the detector fibre 230. One of the fibres, denoted as the source fibre 228, should be situated on the same side of the disc as the electromagnetic beam source. Said source fibre conducts the electromagnetic beam from the source and illuminates a spot of the disc's passing circumference on which the home mark is situated. On the other side of the disc the beams cut-through area is bigger than the cut-through area of the fibre. However, the receiving end of the detector fibre will only receive a well-defined part of the scattered beam. The detector fibre 230 conducts the beam to a transducer arrangement 224 that registers/measures the intensity of the received electromagnetic beam. The transducer arrangement 224 may comprise a electromagnetic transducer and a comparing means. The electromagnetic transducer generates an electric intensity signal including information in relation to the incoming beam intensity. The intensity signal may be a DC signal, of which the output voltage level is depending on the intensity of the incoming beam. The comparing means receives the electric intensity signal from the transducer. The comparing means will compare the intensity information, for instance the output voltage with a threshold value. The comparing means may be designed to provide a "high-level" output signal, e.g. "1" or 5 Volts, when the output voltage exceeds the threshold value, and a "low-level" output signal, for instance "0" or 0 Volt, when the intensity signal is below the threshold value. The level of the threshold value may be adjustable for setting the sensitivity of the detector. The home position mark detector provides an output signal, the detector signal D, to the controller. The output signal of the comparing means may be connected over a conductor 217 to the controller directly or via an interface input/output circuit to the controller. The controller is able to register the changes between the high and low levels, and when they occur in time.

The optical transmission of discs and their home position marks may vary from batch to batch of manufactured discs. Alternatively, the optical transmission of a disc may therefore be scanned, measured/registered and recorded, analogously. The optical transmission may be scanned through a whole disc lap and the threshold value may be adaptively set by the transducer and/or the controller by means of instructions in a controlling program software. The home position mark is located by analyzing the recorded transmission values by using the adaptively set threshold value (instead of a fixed value).

The comparing means may alternatively be included in the controller instead of the transducer arrangement.

Depending on the sensitivity of the detector, everything causing enough influence on the intensity of the beam is possible to register. When scanning the outer circumferential zone of the disc for the home position mark, depending on the pre-set sensitivity, both the home position mark and other marks caused by defects in this zone will be registered. Such defects can be dirt fixed on the disc or defects related to a manufacturing problem of the disc. A home position mark is made during the process of manufacturing the microfluidic disc. Different types of home marks are possible to use. For a microfluidic disc that is injection molded, it is convenient to form the home position mark at the same time as the channel pattern before the lid is fixed on top of the disc base. The home mark may be formed as a grid pattern comprising parallel ducts and ribs laying in a perpendicular direction relatively the rotation direction. When the beam hits within the area of the home position mark, it will be scattered and the beam intensity left after passing the area will be low. However, the quality of each home mark is depending on the prevailing conditions during the manufacture.

Therefore, the sharpness of the borders and beam reducing features may vary from disc to disc.

The present invention and design of the home position mark is not limited to the above described embodiments. All alternative designs of home position marks will therefore land within the scope of the present invention. For instance, no optical transmission or very low optical transmission values may be detected over a disc lap with the exception of the location of the home position mark.

The step of making the home position mark may be performed anytime during the microfluidic disc manufacturing process. For instance, a disc is produced from an optical damping material and the home position mark is a through hole of any kind. Such a hole may be created during the casting of the disc.

When a mark—a home mark or a false mark—is passing the beam, the beam intensity received by the transducer will be reduced. In the case the mark and its border is distinct, the beam intensity changes instantly from high to lower, i.e. low, level when the first leading edge of the mark meets the beam. The received beam intensity will be low until the second, trailing edge of the mark passes the beam and the beam intensity changes from low to high. In the case that the border of a mark is un-sharp, the change from high to low intensity will be extended in time as the intensity will decrease as the incoming beam intensity is fading. The detected position of the edge will depend on the sensitivity and the pre-set detector arrangement threshold value.

The home position detector 208 may detect and react for every trailing edge and/or leading edge of each mark. The detector generates a level change in the detector signal from high to low every time an edge of a mark is detected. The controller receiving the detector signal registers the level change and stores the pulse sum value from a pulse counter means of the controller as a position value/data in a column of a table in a memory connected to the controller. Each pulse sum during the first lap corresponds to a unique position on the disc. Hence, a pulse sum corresponds to a position in a defined direction from the start position. That is an angular distance in a defined direction from the start position $n_p=0$. A certain angular distance is equivalent to the angle of an arc unit multiplied with a certain number of pulses, the pulse sum value $n_p$.

Figure 3:
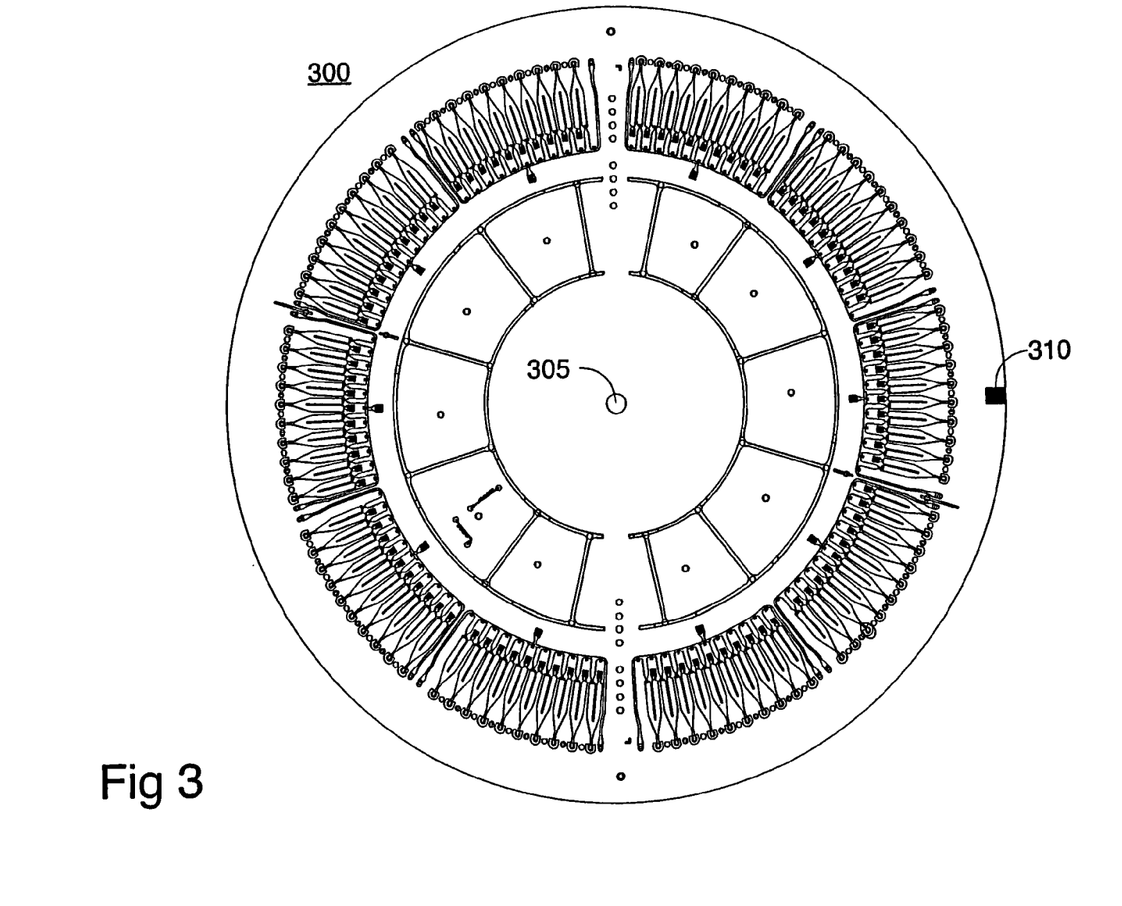
FIG. 3 is a schematic picture of a microfluidic device in form of a disc.

FIG. 3 is a schematic picture of a microfluidic disc 300. A rotatable disc is earlier described e.g. in WO-0146465. The microfluidic device may be made from different materials, such as plastics, glass, silicone polymers, etc. The detector area should be transparent/translucent for the detection principle utilized by the detector. The disc has a central recess 305 for a disc holder. Samples may be placed near the center of the disc and centrifugal forces, created as the disc rotates, may push them out through channels 310 cut into the plastic, circumventing the need to design sophisticated electrokinetic or mechanical pumping structures.

The microfluidic device used in the various aspects of the invention comprises a plurality of microchannel structures in which aliquots of liquids are transported and/or processed. The devices typically are disc-shaped with the microchannel structures oriented in one or more planes. The structures are covered in the sense that their interior is in contact with ambient atmosphere primarily via separate inlet and/or outlet openings and/or vents. Each microchannel structure comprises one or more detection microcavities and possibly also one or more reaction microcavities, and microconduits connecting these parts with each other. A reaction microcavity may coincide with a detection microcavity. The result of the processing in a microchannel structure is measured as radiation from a detection area which is directly or indirectly associated with a detection microcavity. This includes that radiation can be guided within the microfluidic device from a detection microcavity to a part/surface area not directly associated with the microcavity, for instance via an optical fiber.

The microfluidic device may also comprise common channels connecting different microchannel structures, for instance common distribution channels for introduction of liquids and common waste channels including waste reservoirs. Common channels including their various parts such as inlet ports, outlet ports, vents, etc., are considered part of each of the microchannel structures they are connecting. Common microchannels may also connect fluidly groups of microchannel structures that are in different planes. The terms "microchannel", "microconduit", etc., contemplate that a channel structure comprises one or more cavities and/or channels/conduits that have a cross-sectional dimension that is $\leq 10^3$ µm, preferably $\leq 10^2$ µm. The lower limit is typically significantly larger than the size of the largest reagents and constituents of aliquots that are to pass through a microchannel. The volumes of microcavities/microchambers are typically $\leq 1000$ nl, such as $\leq 500$ nl or $\leq 100$ nl or $\leq 50$ nl or $\leq 25$ nl, which in particular applies to the detection microcavities. Chambers/cavities directly connected to inlet ports for liquids may be considerably larger, e.g., microchambers/microcavities intended for application of sample and/or washing liquids. Microformat means that one, two, three or more liquid aliquots that are transported within the device have a volume in the µl-range, i.e., $\leq 1000$ µl such as $\leq 100$ µl or $\leq 50$ µl including but not limited to the nl-range (nanoformat), such as $\leq 1000$ nl or $\leq 500$ nl or $\leq 100$ nl or $\leq 50$ nl. The controller of the microfluidic system has to be able to control and manoeuvre aforementioned needles, pins or detector head to said small cavities with an accuracy of a few µm. The controller has to have the exact position data for different inlet ports, outlet ports, vents, detection positions, etc., of each disc type using the correct home position. Said position data may be stored and possible for the controller to retrieve from the storage, alternatively, the controller may be programmed to calculate the position data. It is therefore very important to find the correct home position mark and to determine the accurate home position on the disc.

Figure 4:
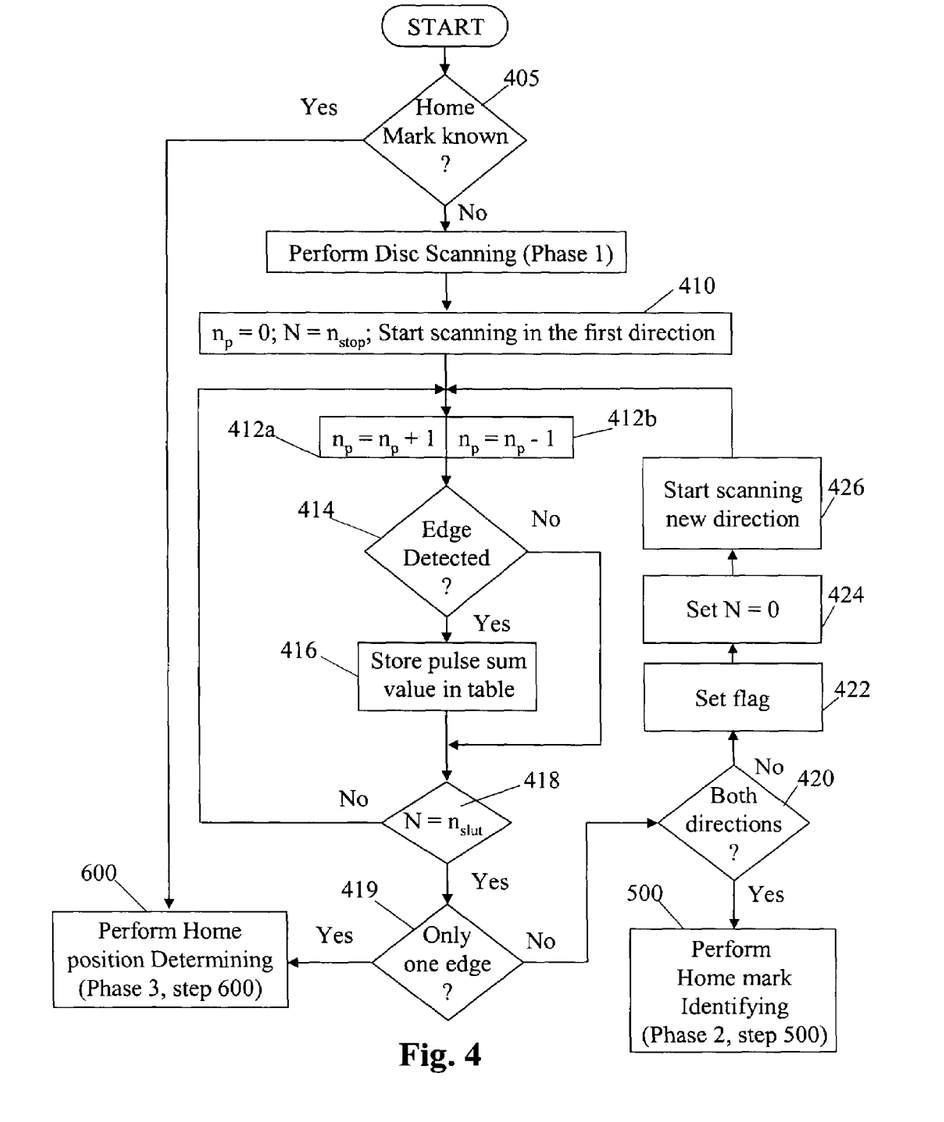
FIGS. 4–6 are flowcharts illustrating an embodiment of the present invented method.
Figure 5:
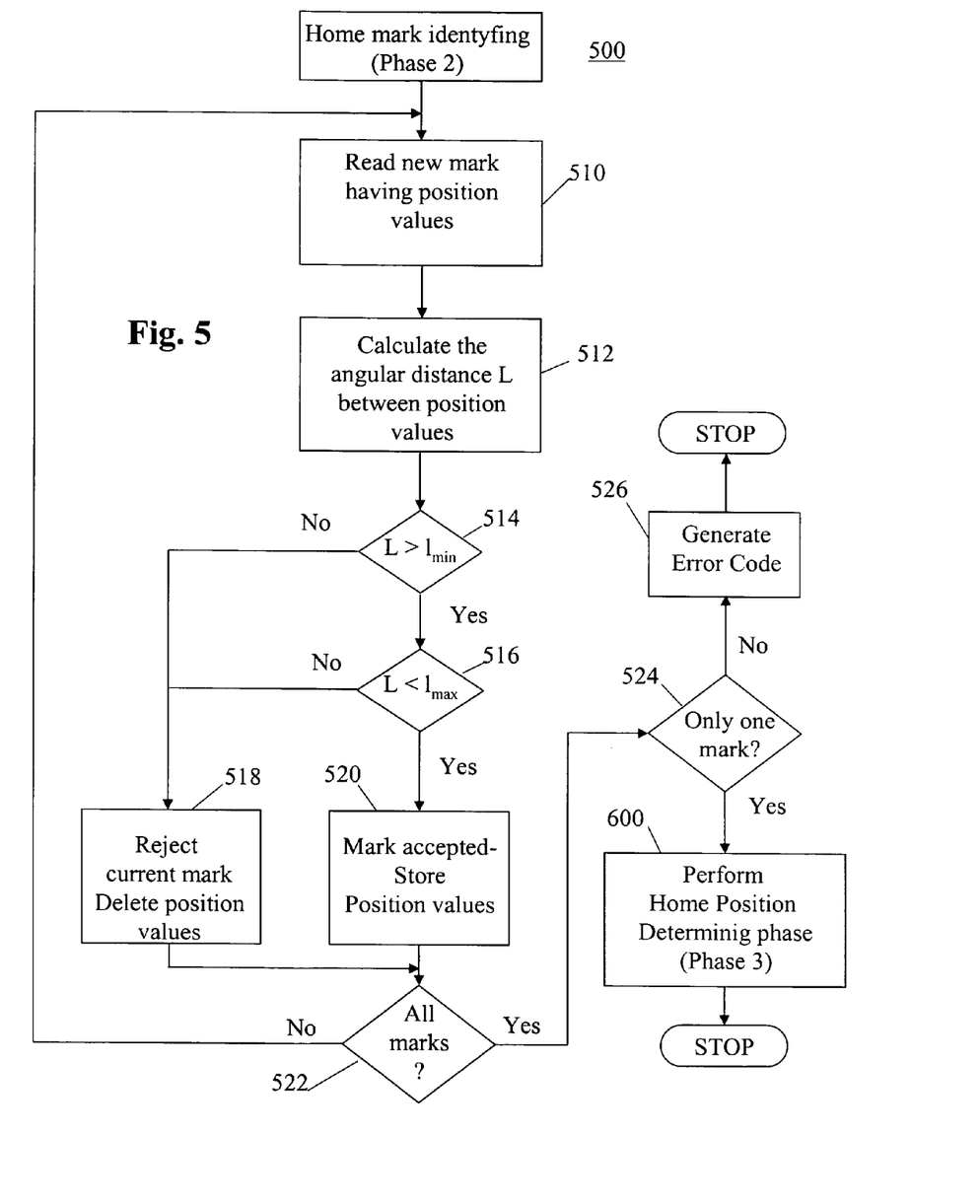
Figure 6:
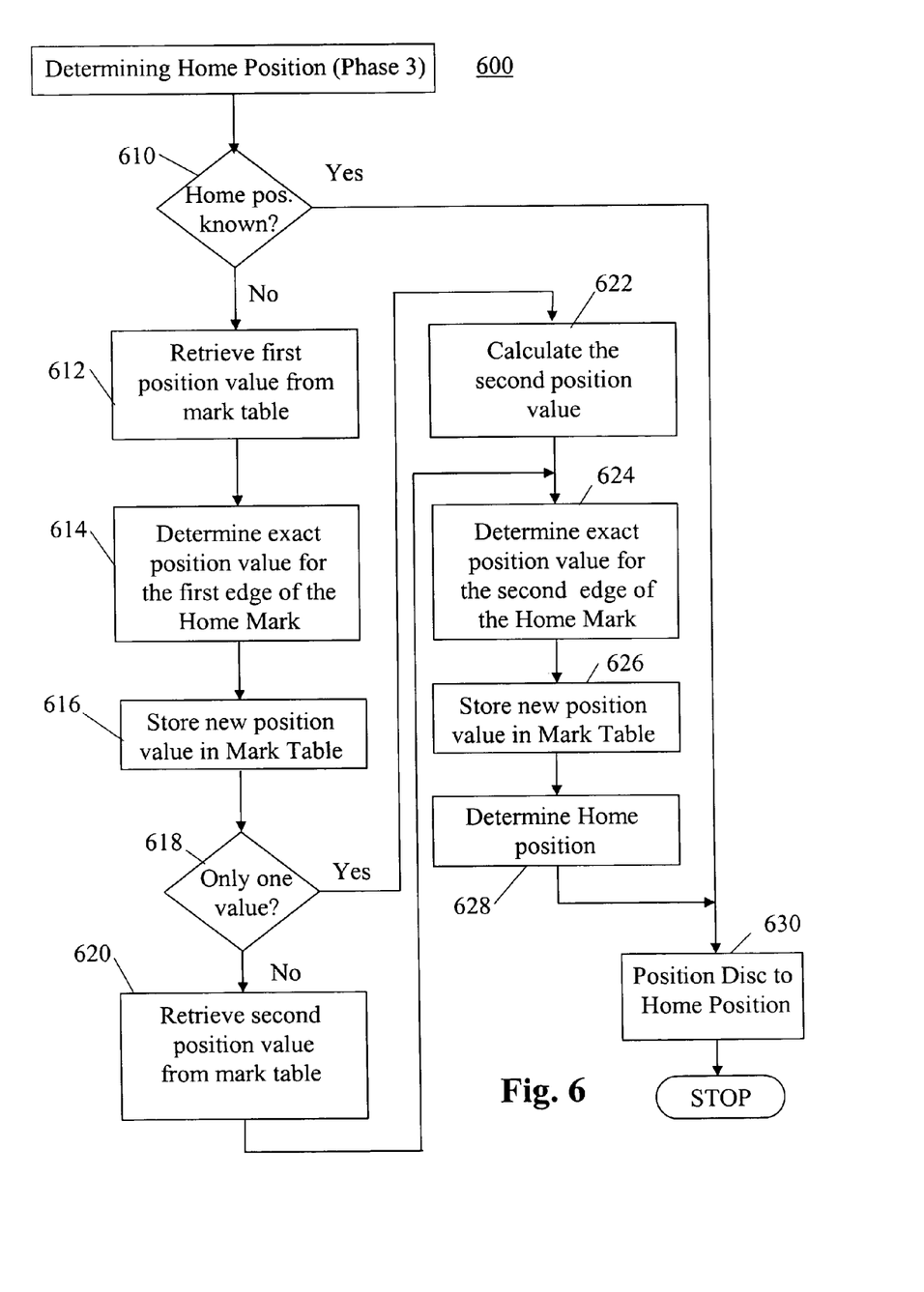

The present invention provides a method for finding the correct home position mark and determining the accurate home position on the current disc laying on the disc holder. The current process is often denoted as the "homing process". FIGS. 4–6 are flowcharts illustrating an embodiment of the invented method.

In this embodiment of the invented method the detector will detect and react for every trailing edge of a mark. In another embodiment of the invented method, the detector is set to detect the leading edge of each mark. In the present embodiment the detector generates a level change in the detector signal from high to low every time a trailing edge of a mark is detected. The controller receiving the detector signal registers the level change and stores the position data stored in the position controlling means of the controller as a position value/data in a column of a table in a memory connected to the controller. Each pulse sum during the first lap correspond to a unique position on the disc. Hence, the position data corresponds to a position in a defined direction from the start position. That is an angular distance in a defined direction from the start position $n_p=0$. A certain angular distance is equivalent to the angle of a resolution grade multiplied with a certain number of pulses, the pulse sum value $n_p$.

When the first phase 400 of the "Homing" process of finding the home position starts, the controller tests, in step 405, if the home position is already known due to the fact that the homing process has been run for the current microfluidic disc. If the home position and the home position mark of the current disc has been determined, the test is positive, yes, and the method continues with step 600, wherein the process continues with phase 3, determining the home position (see FIG. 6). If the "homing process" has not been run for the current disc, the test is negative, no, and the homing process starts with the first phase, the disc scanning. In step 410, a reset signal is generated by the controller to the pulse counter that receives said signal on its reset input and the pulse sum $n_p$ is set to "0" (zero), the stop position N is set to a maximum pulse sum $n_{stop}$ corresponding to a stop position that is preferably located somewhere on the second revolution or lap, and the disc is started to spin in the first direction. A scanning revolution or lap last for more than a single revolution of the disc. The stop value is therefore chosen to be greater than the number of pulses corresponding to exactly one lap. During the disc rotation, a new pulse is generated by the aforementioned encoder for every resolution grade and unit of angular sector movement that a resolution grade represents. The pulse is added to the pulse sum value of the pulse counter in the position controlling means, as in step 412a, if the disc rotates in a first direction, but subtracted from the pulse sum value, as in step 412b, if the disc rotates in a second direction.

In step 414, when a trailing edge has been detected, the controller registers a level change in the detector signal from the home position detector and the controller stores, step 416, the number of pulses corresponding to the position on the disc relatively the start position in a column of a mark table. A first column is filled row by row from the top and downwards. The number of rows filled with a position value corresponds to the number of marks along the arc that the beam scans during the scanning procedure. The last position value in the first column belongs to a mark that will provide the first position value in the opposite direction during the second half of the scanning phase. Therefore, the second column will be filled row by row from the bottom and upwards, as the position values in this column is received during the opposite rotation direction. The last row in the first column is the bottom of the whole table and the first position value of the second lap will be put in the last row. The positions of edges of the same mark will therefore be linked in a correct way.

The scanning procedure will iteratively search all arc unit sectors (an arc unit sector corresponds to the angular distance of a resolution grade) for new trailing edges. In step 418, the sum $n_p$ is compared to the stop value N that corresponds to the stop position. Therefore, the disc will rotate a predetermined scanning distance, for an example 10% of a lap, further beyond said start position until the stop criteria in step 418 is fulfilled, yes, and the disc rotation stops.

The next moment of the scanning process is to scan the disc in the opposite direction to find the other edge of each mark that was registered during the first scanning lap.

However, if only one edge has been detected during the first scanning revolution, this edge probably belongs to the border of the home mark because the circumferential zone where the home position mark is placed has no defects. In step 419, it is tested if only one edge is detected. If the test is positive, yes, the method continues with step 600, wherein the process continues with phase 3, determining the home position (see FIG. 6). If instead the test is negative, no, the method continues testing if the disc already has been rotated in both directions before starting the disc rotation in the opposite direction. Such a test is performed in step 420. A flag in a special memory address indicates that both directions has been scanned. Said test in step 420 occurs when a scanning lap is finished and indicates, if the flag is absent, that only one direction is finished and a second lap has to be scanned.

The flag is set, step 422, the stop value N is set to zero, step 424, and the second scanning in the other direction starts as the controller initiates the motor to rotate the disc in the other direction, step 426. The stop criteria is set to zero, because the disc rotates in the opposite direction and the pulse counter of the position controller means will therefore count down from the maximum value to zero. Thus, the pulse counter counts down and for each arc unit sector scanned the pulse sum is decreased with one unit, step 412b. As soon as a trailing edge is detected in an arc unit sector, a level change is detected in the detector signal by the controller and the pulse sum of the pulse counter is read and stored in the table, step 416. The scanning process proceeds until the counter pulse sum fulfils the stop criteria, yes, step 418. As soon as the pulse sum $n_p$ is zero the central processor stops the rotation and scanning. The beam lands exactly on the original start spot on the disc. The disc has been rotated in both directions, and as the flag was set when the second scanning lap started, the flag indicates that both directions has been scanned and the criteria in step 420 is fulfilled (yes). The second phase of the process, to identify which mark is the true home position mark, can start, step 500 in FIG. 5.

In FIG. 5 the algorithm of the process of identifying the home mark, denoted as the second phase, 500, is illustrated. The second phase starts with step 510, in which the processing unit reads the two first position values, one from each column but in the same row. In the next step, step 512, the controller calculates the angular distance L between the position values. The distance will be compared to a minimum distance value $l_{min}$, in step 514. If L doesn't exceed $l_{min}$, the condition L>$l_{min}$ is false (no). That mark is not the home position mark and such false marks are rejected, step 518. If instead the condition in step 514 is true, yes, which occur when the angular distance L is longer than the minimum distance $l_{min}$. There is a chance that the mark is the correct home position mark. In step 516, the calculated angular distance L is compared to a maximum distance value $L_{max}$. If the condition is false, no, because L>$l_{max}$, the mark has to be a false mark and each such a mark is rejected in step 518 of the process. Each time a mark is found to be false in one of the test steps 514, 516, the position values of that mark are deleted in the table and a new pair of position values is read from the table. The criteria of step 522 keeps the iterative process running until all pair of position values have been investigated. Therefore, the process continues with step 510, wherein the processor reads a new pair of position values. If both conditions in steps, 514 and 516, are true, this mark is a possible home position mark and the position values are saved and stored, as done in step 520. When all position values have been investigated, the condition of step 522 is true, yes, and the iterative process is stopped. There will be only one pair of position values left if the conditions of steps 514 and 516 are tight enough. In step 524, it is tested if there is more than one pair of position values left or no pair of position values at all. If there is more than one pair of position values left or no pair of position values at all, yes, the controller will generate and display an error code, step 526. That means that current disc is not acceptable and it is no use to continue the homing process. The disc has to be discarded. If the test in step 524 is positive, the homing process can continue with step 600 (see FIG. 6)

When there is left only one single pair of position values whose angular distance L fulfils the "window" criteria of steps 514 and 516. These position values are used for calculating the home position, or origin, for the local coordinate system of that microfluidic disc. The home position may be defined anywhere on or between the two position values of the home mark. As an example and embodiment of the present invention, the home position can be defined to be located in the middle between the home mark position values.

The third phase of the preferred embodiment of the present invention will now be described in more detail in association with FIG. 6. This phase of the process determines the exact position of the home location.

The first step of the method 600, is to check, in step 610, if the method for finding the home position already has been used for the present microfluidic disc and if there already exists a exact home position. This could be done if a flag is set in a certain storage address every time the present method has been run. An alternative test is to check if there is a position value present. If a flag is present or a home position value is present (the home position parameter has a value greater than zero), the condition in step 610 is fulfilled, yes, and method will proceed to step 630, in which the disc is positioned in the home position.

If the condition is not fulfilled, no, the method retrieves the first position value from the mark table, step 612. The controller will determine exact position value for this first edge, step 614, by only scanning the area surrounding the retrieved position slower than during the first phase of the method. A new threshold value increasing the methods sensitivity might be set by the controller and used in the detector, however, this could be optional. The new position value replaces the old position value in the mark table, step 616, even though they don't differ.

When the disc has no other marks than the home position mark, the scanning of phase one will only be performed in one scanning direction. Therefore, only one edge of the home position mark has been detected and the mark table will only contain one single position value. In step 618, it is tested if the mark table only contains one position value.

If the condition in step 618 is not fulfilled, no, the controller retrieves the second position value from the mark table, step 620. The controller will determine exact position value for this second edge, step 624, by only scanning the area surrounding the retrieved position slower than during the first phase of the method. A new threshold value increasing the methods sensitivity might be set by the controller and used in the detector, however, this could be optional. The new position value is stored and replaces the old position value in the mark table, step 626, even though they don't differ.

If the condition in step 618 is fulfilled, yes, the method performs step 622, wherein the second position value is calculated by retrieving the first position value from the mark table and adding the angular distance, $L_{home}$, of a standard home position home mark to this first position value from the mark table. The controller will use this calculated value for the second position value when determining the exact position value for this second edge, step 624, by only scanning the area surrounding the calculated position. The new position value will be stored as the second position in the mark table, step 626.

The two edges of the home mark position are now known. In step 628, these position values is used for calculating the home position, or origin, for the local coordinate system of that microfluidic disc. The home position may be defined anywhere on the outer circumferential zone of the disc, but preferably the home position is placed on or between the two position values of the home mark. As an example and embodiment of the present invention, the home position can be defined, in step 628, to be located in the middle between the home mark position values. E.g., the home position $N_{home}$ may be calculated by use of the formula $$N_{home} = \frac{n_p + n_p + L}{2}. \quad (1)$$

Finally, when the home position is known, the disc is rotated so the beam of the home position detector hits the home position, step 630.

As stated above, different position devices such as encoders, absolute position encoders etc may be used. Therefore, some steps of the invented method has to be modified.

Another embodiment of the invented method is hereafter presented. This embodiment is adapted for systems using an absolute encoder as a position device. This type of device progressively gives the angular distance from the home position mark while the disc is rotating. Therefore, some steps of the first embodiment has to be modified. Step 412a and b can be discarded. In step 416 of the first embodiment, the pulse sum will not be stored. In the modified method, an angular distance from the home position mark will be stored. A new stop criterion has to be defined for step 418. By using calculating means, included for instance in the position controlling means (220 in FIG. 2), the predetermined scanning distance from a arbitrary start position to the stop position can be calculated as the time needed from a preset rotation speed and the angular distance between the start position and stop position (i.e., from the preset rotation speed and the angular position co-ordinate). The disc is scanned the predetermined scanning distance when a time parameter t, measuring the running time from scanning start, equals the calculated stop time $T_{stop}$. The other steps of the first embodiment may remain unmodified in this second embodiment.

The present invention may be implemented as a computer program product directly loadable into an internal memory storage of a processing unit within the controller in the microfluidic system, comprising the software code means for performing the steps of any claims 1–9.

Further, the present invention relates to a computer program product stored on a computer usable medium, comprising readable program for causing a processing unit in a computer means to control an execution of the steps of any of the claims 1–9.

The computer usable medium is a record medium, a computer memory, a Read-Only Memory or an electrical carrier signal.

The present invention is not limited to the above-described preferred embodiments. Various alternatives, modifications and equivalents may be used. Therefore, the above embodiments should not be taken as limiting the scope of the invention, which is defined by the appended claims.

What is claimed is:

1. A method for determining a home position by means of a home position mark on a microfluidic device used in a microfluidic system comprising at least one programmable controller having storage means, a position device being able to communicate with the controller, and a home position mark detector connected to said controller, wherein said method comprises the following steps:
   scanning a disc for mark edges;
   rejecting false home mark(s) and identifying a correct home position mark; and
   determining a home position by use of mark edges of the correct home position mark identified in the previous step.

2. The method according to claim 1, wherein the method comprises the following steps:
   scanning and detecting mark edges on the microfluidic device, which is rotating in a first direction and a predetermined scanning distance from an arbitrary start position on the microfluidic device;
   storing in the storage means position value(s) corresponding to mark edges being detected by the home position mark detector during said rotating;
   stopping the scanning in the first direction of the microfluidic device, when the microfluidic device has rotated the predetermined scanning distance from the arbitrary start position;
   scanning and detecting mark edges on the mark fluidic device when the device is rotating in a second direction; and
   determining the home position by means of two positions defined by the home position mark.

3. The method according to claim 1, wherein the home position mark is identified by means of a min-max window.

4. The method according to claim 1, wherein the mark edges are a leading edge.

5. The method according to claim 1, wherein the mark edges are a trailing edge.

6. The method according to claim 1, wherein the step of rejecting false home mark(s) and identifying the correct home position mark comprises the step of:
   comparing an angular distance L of a mark to a minimum distance $1_{min}$ and rejecting the mark if L is not exceeding $1_{min}$.

7. The method according to claim 1, wherein the step of rejecting false home mark(s) and identifying the correct home position mark comprises the step of:
   comparing an angular distance L of a mark to a maximum distance $1_{max}$ and rejecting the mark if L is exceeding $1_{max}$.

8. The method according to claim 1, wherein the method also comprises the step of:
   calculating the home position by use of position values for the mark edges of the identified correct home position mark, wherein the home position may be defined anywhere on or between the position values of the mark edges.

9. The method according to claim 1, wherein the step of rejecting false home mark(s) and identifying the correct home position mark comprises the step of:
   comparing the angular distance L of a mark to a maximum distance $1_{max}$ and a minimum distance $1_{min}$, and rejecting the mark if L is exceeding $1_{max}$, or if L is less than $1_{min}$.

10. A method for locating a home position mark of a microfluidic device used in a microfluidic system comprising at least one central processor and storage means for computer program code, and an encoder being able to generate encoder pulses corresponding to a predefined resolution of the microfluidic device into a number of arc unit sectors, wherein each arc unit sector corresponds to an encoder pulse and each specific number of encoder pulses, a pulse sum ($n_p$), represents a specific angular position in a first direction relatively a start position ($n_p=0$), said method comprises following steps of:
   scanning the microfluidic device, which is rotating in a first direction;
   adding an encoder generated pulse for each arc unit sector passing a detector to an encoder pulse sum in a pulse counter;
   detecting in each arc unit sector passing the detector if a mark edge is present in the sector;
   storing in a mark table each pulse sum $n_p$ as a position value corresponding to each arc unit sector wherein a mark edge is detected;
   stopping the scanning of the first direction of the microfluidic device, when the value of the pulse sum $n_p$ is equal to or exceeds a value N;
   rotating and scanning the microfluidic device in a second direction opposite to the first direction;
   detecting in each arc unit sector passing the detector if a mark edge is present in the sector;
   storing in the mark table each pulse sum $n_p$ as a position value corresponding to each arc unit sector wherein a mark edge is detected;
   stopping the scanning of the second direction of the microfluidic device, when the value of the encoder pulse sum is equal to a zero;
   calculating an angular distance L between position values for each of the marks stored in the mark table; and
   identifying the home position mark by means of a min-max window.

11. A computer program product directly loadable into an internal memory storage of a processing unit within the computer means comprising the software code means for performing the steps of claim 1.

12. A computer program product stored on a computer usable medium, comprising readable program for causing a processing unit in a computer means to control an execution of the steps of claim 1.

13. The computer program product according to claim 12, wherein the computer usable medium is a record medium.

14. The computer program product according to claim 12, wherein the computer usable medium is a computer memory.

15. The computer program product according to claim 12, wherein the computer usable medium is a Read-Only Memory.

16. The computer program product according to claim 12, characterised in the computer usable medium is an electrical carrier signal.

17. A microfluidic system comprising at least one microfluidic instrument controlled by a programmable controller having storage means, a position device being able to communicate with the controller, a home position mark detector connected to the controller and a computer program product, wherein the microfluidic instrument is capable of handling different microfluidic device(s), each microfluidic device has a home position mark thereon, and the computer program product is directly loadable into an internal memory storage of a processing unit within the controller, causing the controller to be able to perform a method comprising the following steps:

scanning a disc for mark edges;

rejecting false home mark(s) and identifying a correct home position mark; and determining a home position by use of exactly determined edges of the home position mark.

18. The system according to claim 17, wherein the home position mark detector comprises means being able to detect a home position mark on a microfluidic device.

19. The system according to claim 17, wherein the home position mark detector comprises an electromagnetic beam source and a transducer arrangement.

20. The system according to claim 17, wherein the controller comprises a position controlling means that is able to receive or transmit different data using a position signal P over a connection between the controller and the position device.

21. The system according to claim 17, wherein the position device is an encoder generating a pulse for each resolution grade and the position controlling means involves a pulse counter for registering the pulse sum value that is representing the current position of the disc relative to a start position or the home position and the detector.

22. The system according to claim 17, wherein the position device is an absolute encoder, and the position controlling means will receive or transmit an absolute measure of the angular distance from a start position or the home position.

23. A computer program product directly loadable into an internal memory storage of a processing unit within the computer means comprising the software code means for performing the steps of claim 10.

24. A computer program product stored on a computer usable medium, comprising readable program for causing a processing unit in a computer means to control an execution of the steps of claim 10.

25. The computer program product according to claim 24, wherein the computer usable medium is a record medium.

26. The computer program product according to claim 24, wherein the computer usable medium is a computer memory.

27. The computer program product according to claim 24, wherein the computer usable medium is a Read-Only Memory.

28. The computer program product according to claim 24, characterised in the computer usable medium is an electrical carrier signal.

\* \* \* \* \*